United States Patent [19]

Crowley

[11] Patent Number: 4,898,580

[45] Date of Patent: Feb. 6, 1990

[54] SYRINGE FOR A LIQUID PHARMACEUTICAL COMPOSITION

[75] Inventor: Patrick J. Crowley, Epsam, England

[73] Assignee: Beecham Group p.l.c., Middlesex, England

[21] Appl. No.: 253,677

[22] Filed: Oct. 4, 1988

[30] Foreign Application Priority Data

Oct. 6, 1987 [GB] United Kingdom ............... 8723454

[51] Int. Cl.[4] .................................................. A61M 5/00
[52] U.S. Cl. ...................................... 604/90; 604/191; 206/204
[58] Field of Search .................. 604/82, 88–90, 604/92, 191, 56, 416, 403, 404; 206/204

[56] References Cited

U.S. PATENT DOCUMENTS

| | | | |
|---|---|---|---|
| 2,477,926 | 8/1949 | Greaves | 604/404 |
| 2,842,223 | 7/1958 | Zall | 206/204 |
| 3,343,897 | 9/1967 | Keller | 206/204 |
| 3,459,185 | 8/1969 | Bender et al. | 604/404 |
| 3,739,947 | 6/1973 | Baumann et al. | 604/89 |
| 3,833,406 | 9/1974 | White | 206/204 |
| 4,545,492 | 10/1985 | Firestone | 206/204 |
| 4,599,082 | 7/1986 | Grimard | 604/90 |
| 4,613,326 | 9/1986 | Szwarc | 604/89 |
| 4,716,710 | 1/1988 | Galey et al. | 604/226 |

Primary Examiner—Dalton L. Truluck
Assistant Examiner—Denise W. DeFranco
Attorney, Agent, or Firm—Hopgood, Calimafde, Kalil, Blaustein & Judlowe

[57] ABSTRACT

A syringe for dispensing a liquid pharmaceutical composition has a first chamber (5), adjacent to nozzle (3), which contains a mositure sensitive solid drug, two movable septa (8,9) which together create a second chamber (6) and a third chamber (7) holding a liquid diluent, and a liquid by-pass passage (19) which can connect the third chamber (7) to the first chamber (5) while by-passing second chamber (6).

A plunger (4) is depressed to move the septum (9) towards the nozzle (3), thereby causing liquid diluent to flow via by-pass passage (19) into the first chamber (5) to mix with the drug.

The second chamber (6) contains moisture sequestering material to insulate the drug from any moisture which might leak through septum (9).

7 Claims, 1 Drawing Sheet

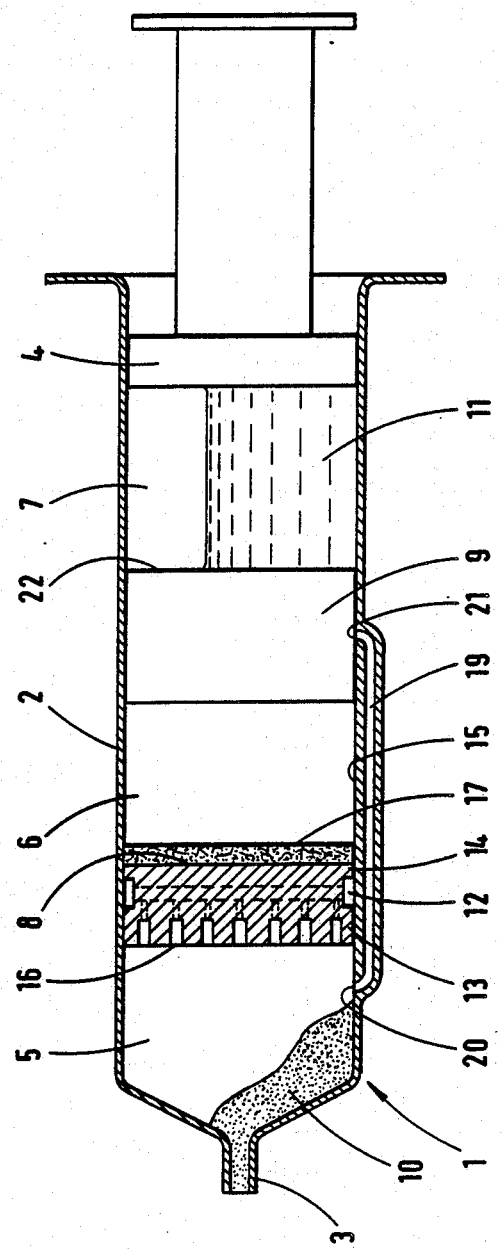

SYRINGE FOR A LIQUID PHARMACEUTICAL COMPOSITION

The present invention relates to a syringe for administering a liquid pharmaceutical composition to a human or non-human subject, particularly for administering a composition which includes a moisture sensitive component.

It is often necessary to mix a moisture sensitive drug with an aqueous diluent just prior to administration of the final composition, especially when the drug is susceptible to deterioration when exposed to even small traces of moisture. Parenteral administration of such a composition using a conventional syringe system is generally only possible if the composition is first made up from the separate components and subsequently transferred to the syringe.

A novel syringe has now been devised in which the moisture sensitive component can be retained, separated from the diluent by barriers which prevent the leakage of moisture from the diluent to the component, and in which mixing of the diluent and component can occur merely by actuation of the syringe plunger, in a conventional manner. The syringe of the invention will therefore be ready for use by the medical practitioner without separate preparation of the pharmaceutical composition and transfer to the syringe.

According to the present invention there is provided a syringe for dispensing a liquid pharmaceutical composition, comprising a first chamber, adjacent the syringe outlet, for holding a first moisture sensitive component of the composition, a second chamber, adjacent the first chamber, containing moisture sequestering material, the second chamber being separated from the first chamber by a first barrier member movable within the syringe in response to fluid pressure, a third chamber, separated from the second chamber by a further movable barrier member, for holding a second, liquid component of the composition and being closed by a syringe plunger, and a liquid by pass for connecting the liquid component in the third chamber to the moisture sensitive component in the first chamber when the further movable barrier reaches a predetermined position in the syringe in response to a compressive force from the plunger.

Preferably, the first barrier member comprises resilient rubber or plastics having desiccant properties, provided either by incorporating desiccant material into the member or by drying the member at a high temperature.

The second chamber may contain moisture sequestering material in the form of a disc of similar diameter to that of the internal wall of the syringe. The disc may be attached to either of the barrier members, or may be freely movable in the second chamber. Alternatively, moisture sequestering material may be coated onto the internal wall of the syringe.

Any other method of retaining sequestering material within the second chamber may be used, provided the chamber preserves an atmosphere essentially free of moisture.

The further barrier member may consist of the same resilient material as the first member, and is advantageously of greater axial length than the first barrier member. This will reduce the risk of a liquid component in the third chamber leaking through into the second chamber, thereby causing deterioration of the moisture sequestering material.

The liquid by-pass preferably comprises a tubular passage either built into the wall of the syringe or projecting out of and extending parallel to the wall.

Prior to movement of the barrier members due to compressive force from the plunger, one end of the by-pass conveniently faces the wall of the further barrier, so that initially liquid cannot pass from the third chamber into the first chamber, while the other end of the by-pass opens into the first chamber.

On pushing the plunger into the syringe, the liquid component exerts a fluid pressure against the further member and causes the latter to move towards the syringe outlet, thereby enabling the said one end of the by-pass to open out into the third chamber. The liquid component can then be forced down the by-pass towards the other end thereof.

In one embodiment of the invention, the first barrier member is designed to move towards the syringe outlet simultaneously with the further member so that when liquid component flows through the by-pass it meets the wall of the first member instead of flowing directly into the first chamber. The wall may be formed with a circumferential channel connected to circumferentially spaced axially aligned grooves leading to the first chamber, so that liquid entering the channel from the by-pass can be distributed into the first chamber in a rate controlled manner, according to the size and distribution of the grooves thereby enabling the liquid component to mix thoroughly with the moisture sensitive component before the final composition is ejected from the outlet.

Preferably, the moisture sensitive component comprises a pharmaceutically active material such as an antibiotic or a cardiovascular agent. Examples of the latter are anistreplase (marketed by Beecham Group p.l.c. under the trade mark of EMINASE) and TPA (tissue plasminogen activator). The active agent can advantageously have the form of a solid cake of freeze dried material Any drug material which can be diluted with a liquid component prior to administration as a liquid composition may be used in the syringe of the invention. The syringe may be used to deliver a pharmaceutical composition by the parenteral route (eg. intravenous, intramuscular or subcutaneous) to a human or non-human animal.

The invention is now described with reference to the accompanying drawing, which is a vertical section through a syringe.

Referring to the drawing, a syringe 1 consists of a tubular barrel 2 having an outlet nozzle 3 and a plunger 4. The interior of the barrel 2 is separated into a first chamber 5, a second chamber 6 and a third chamber 7 by means of a first barrier member 8 and a further barrier member 9. The first chamber 5, adjacent nozzle 3, contains a solid moisture sensitive drug 10, while the third chamber 7 contains an aqueous diluent 11 which is intended to mix with drug 10 to form an aqueous solution suitable for injecting into an animal body.

The first barrier member 8 consists of a rubber septum which may be heat treated to provide desiccating properties, the septum having a circumferential channel 12 formed by walls 13 and 14 which are in tight sealing engagement with the internal wall 15 of the syringe 1. The channel communicates via circumferentially spaced, axially aligned grooves 16 with the first chamber 5, to enable liquid entering the channel 12 to be distributed in a controlled manner through the grooves 16 into the chamber 5.

The second chamber 6 contains a disc 17 of moisture sequestering material, such as a molecular sieve of hydroxyethyl metacrylic acid polymer (HEMA), which has the same diameter as the internal wall 15, the disc being located adjacent the septum 8. The chamber 6 is sealed by means of the further barrier member 9 which is in the form of a cylindrical rubber septum of greater axial length than septum 8. The chamber 6 accordingly has a moisture sequestering function, which reduces the risk of moisture leaking into the chamber 5 from chamber 7 via the interface between septa 8 and 9 and the wall 15.

liquid by-pass in the form of a narrow tubular passage 19 connects the chamber 5, at passage exit 20, to the wall of the septum 9 at passage entrance 21 so that diluent 11 is initially prevented from contacting the drug 10 in the chamber 5.

In use, force on the plunger 4 causes hydrostatic pressure, transmitted through the diluent 11, to move the septum 9 towards the nozzle 3 until the rearmost face 22 of the septum 9 reaches the passage entrance 21. At the same time as septum 9 moves, septum 8 also moves under fluid pressure towards nozzle 3 so that when the face 22 reaches the passage entrance 21, the channel 12 communicates with the passage exit 20. Continuing pressure on the plunger 4 forces diluent 11 through the passage 19 into the channel 12 of the septum 8, where it is distributed to the drug 10 via grooves 16. Further movement of the plunger 4 results in the liquid drug composition issuing from the nozzle 3, from which it can be injected via a hollow needle (not shown).

In order to prevent moisture entering the chamber 5 through the nozzle 3, the latter can be sealed by a cap (not shown) having the same desiccant properties as the septum 8, the cap being either a tight push fit on the nozzle, or a screw fit.

What is claimed:

1. A syringe for dispensing a liquid pharmaceutical composition, comprising a first chamber, adjacent the syringe outlet, for holding a first moisture sensitive component of the composition, a second chamber, adjacent the first chamber, containing moisture sequestering material, the second chamber being separated from the first chamber by a first barrier member movable within the syringe in response to fluid pressure, a third chamber, separated from the second chamber by a further movable barrier member, for holding a second, liquid component of the composition and being closed by a syringe plunger, and a liquid by pass around and outside the second chamber, for connecting the liquid component in the third chamber when the further movable barrier member reaches a predetermined position in the syringe in response to a compressive force from the plunger.

2. A syringe according to claim 1, in which the first barrier member comprises resilient rubber or plastics material having desiccant properties.

3. A syringe according to claim 1, in which the second chamber contains moisture sequestering material in the form of a disc of similar diameter to that of the internal wall of the syringe.

4. A syringe according to claim 1, in which the further barrier member is of greater axial length than the first barrier member.

5. A syringe according to claim 1, in which the liquid by-pass comprises a tubular passage built into the wall of the syringe or projecting out of and extending parallel to the wall.

6. A syringe according to claim 1, in which the first barrier member has a circumferential wall formed with a circumferential channel connected to axially aligned grooves leading to the first chamber.

7. A syringe according to claim 1, containing a moisture sensitive, pharmaceutically active solid material in the first chamber.

* * * * *

UNITED STATES PATENT AND TRADEMARK OFFICE
CERTIFICATE OF CORRECTION

PATENT NO. : 4,898,580
DATED : February 6, 1990
INVENTOR(S) : Patrick J. Crowley It is certified that error appears in the above-identified patent and that said Letters Patent is hereby corrected as shown below:

In Claim 1, line 14, after the word "chamber" insert -- to the moisture sensitive component in the first chamber --.

Signed and Sealed this

Twelfth Day of February, 1991

*Attest:*

HARRY F. MANBECK, JR.

*Attesting Officer*     *Commissioner of Patents and Trademarks*